(12) United States Patent
Gomez

(10) Patent No.: US 7,255,107 B1
(45) Date of Patent: Aug. 14, 2007

(54) NASAL MASK ASSEMBLY FOR NASAL DELIVERY

(76) Inventor: Roy C. Gomez, 537 Linwood Dr., Richlands, VA (US) 24641

( * ) Notice: Subject to any disclaimer, the term of this patent is extended or adjusted under 35 U.S.C. 154(b) by 512 days.

(21) Appl. No.: 10/686,268

(22) Filed: Oct. 14, 2003

(51) Int. Cl.
- A62B 18/02 (2006.01)
- A61M 15/08 (2006.01)
- A61M 16/00 (2006.01)

(52) U.S. Cl. ............. 128/207.13; 128/206.11; 128/207.18

(58) Field of Classification Search ........... 128/203.12, 128/204.18, 205.25, 206.11, 206.12, 206.13, 128/206.14, 206.18, 206.21, 206.24, 207.11, 128/207.13, DIG. 26

See application file for complete search history.

(56) References Cited

U.S. PATENT DOCUMENTS

| | | | | |
|---|---|---|---|---|
| 4,354,488 A | * | 10/1982 | Bartos | 128/205.25 |
| 4,944,310 A | * | 7/1990 | Sullivan | 128/848 |
| 5,348,000 A | | 9/1994 | Teves | 128/204.18 |
| 5,537,994 A | | 7/1996 | Thornton | 128/204.18 |
| 5,918,598 A | * | 7/1999 | Belfer et al. | 128/206.25 |
| 6,012,455 A | | 1/2000 | Goldstein | 128/207.18 |
| 6,192,886 B1 | | 2/2001 | Rudolph | 128/207.13 |
| 6,418,928 B1 | * | 7/2002 | Bordewick et al. | 128/205.25 |
| 6,860,268 B2 | * | 3/2005 | Bohn et al. | 128/206.21 |

* cited by examiner

*Primary Examiner*—Justine R. Yu
*Assistant Examiner*—Annette Dixon
(74) *Attorney, Agent, or Firm*—Thompson Hine LLP

(57) ABSTRACT

A nasal mask assembly is configured to provide a direct flow of a fluid, e.g., breathable air, oxygen or anesthesia, directly into the patient's nasal cavity by combining the nasal prongs of a nasal cannula with a nasal cup. The nasal cup is made of clear plastic and has a general shape of a human nose such that it easily and comfortably fits over a patient's nose. An input port extends through the nasal cup into the internal cavity of the nasal cup and a fluid source is connected to the input port via a source tube system. The nasal cup can be molded to approximate the surface of a patient's face surrounding the patient's nose. The nasal prongs are extended in length. The source tube is rotatably connected to the external end of the input port of the nasal cup.

34 Claims, 6 Drawing Sheets

NASAL MASK ASSEMBLY FOR NASAL DELIVERY

BACKGROUND OF THE INVENTION

1. Field of the Invention

This invention relates to nasal masks for delivering oxygen to a patient, and in particular, to nasal masks having nasal prongs.

2. Related Art

Patients today needing a continuous flow of oxygen, whether in a hospital or for home use, are limited as to the type of apparatuses available. At present, a patient receives oxygen through a conventional nasal cannula, see FIG. 1A showing the Prior Art, wherein oxygen is delivered to the patient's nostrils through a pair of one half inch long nasal prongs extending from a thin tubing—one prong being inserted in each nostril. The two ends of the thin tubing of the nasal cannula are connected to an oxygen source by a predefined length of conventional, thicker tubing. The nasal cannula is held in place on a patient by the thin tubing which is hung, or looped, around the patient's neck or ears. The nasal cannula is further held in place by sliding a small piece of plastic attached to the thin tubing toward the patient's head and neck, wherein both ends of the thin tubing are inserted through the piece of plastic. As the piece of plastic gets close to the patient's head and neck, the tighter the tubing becomes, thereby holding the nasal prongs within the patient's nostrils. The piece of plastic is held in position on a desired point of the thin tubing of the nasal cannula by friction.

There are many disadvantages with a conventional nasal cannula. First, the nasal prongs are only one half of an inch in length. Although this short length appears to be for the comfort of the patient, it is very inefficient in the delivery of oxygen. That is, because the nasal prongs are so short, the nasal prongs do not fit well within a patient's nostrils such that part of the oxygen escapes out of the patient's nostrils.

Second, the short length of the nasal prongs causes the nasal prongs to fall out of the patient's nostrils very easily. This is especially true when a patient makes the slightest turn of his/her head.

Third, the fastening mechanism of a conventional nasal cannula is very weak. The nasal cannula is held in place by simply looping the thin tubing around the patient's neck or ears and sliding a small piece of plastic into place. As a result, the nasal prongs are easily pulled out of the patient's nostrils, which typically happens during sleep.

Accordingly, conventional nasal cannulas are very ineffective because patients do not receive oxygen in the same concentrations as needed. Therefore, there is a need for a nasal mask assembly that provides a patient with a continual and constant flow of oxygen in the needed concentration. There is a further need for a nasal mask assembly using nasal prongs that is flexible and capable of maintaining its position on a patient even when the patient moves and turns his/her head.

Several United States patents attempted to solve the problems associated with delivering oxygen, or other fluid, e.g., breathable air or an anesthesia, to a patient. However, none of these prior patents provide a simple solution for a patient, and all of these prior art patents are cumbersome and very intrusive to a patient. For example, in U.S. Pat. No. 5,348,000 ("the '000 patent"), an apparatus is disclosed having an interchangeable facemask and nasal catheter. That is, a facemask is inserted in the flow of fluid, e.g., anesthesia, between an anesthesia machine and the nasal prongs of a nasal catheter. With this arrangement, a physician can switch easily between using the nasal catheter and a facemask on a patient without having to reconfigure the anesthesia machine.

Although the '000 patent benefits physicians during minor surgeries, the apparatus of the '000 patent does not provide any advantage to a patient requiring a constant and uninterrupted flow of oxygen. A patient would have to choose between using the nasal prongs of a conventional nasal catheter or the face mask. There is absolutely no way that a patient would be able to use both the nasal prongs with the face mask. Thus, a patient experiences the same disadvantages with the apparatus of the '000 patent that he/she experiences using a conventional nasal cannula.

In U.S. Pat. No. 5,537,994 ("the '994 patent"), a combination face mask and dental device is disclosed to improve a person's breathing during sleeping. The dental device is attached to the face mask such that the dental device acts as an anchor to maintain the placement and position of the face mask on the patient. As with other devices, the face mask is connected to a constant positive air pressure (CPAP) system by conventional means. There are several obvious disadvantages with the device of the '994 patent: a patient could only use this device while sleeping because it would interfere with talking and eating; the dental device is very cumbersome and awkward to use; and there is no direct flow of air into the patient's nostrils.

In U.S. Pat. No. 6,012,455 ("the '455 patent"), another dentally stabilized nasal mask is disclosed. The device is functionally similar to the device of the '994 patent, and thus, suffers from the same disadvantages.

In U.S. Pat. No. 6,192,886 ("the '886 patent"), a nasal mask is disclosed having sealing flanges extending around the rim for forming an air-tight seal during use. The principal disadvantage of this nasal mask is that it requires the patient to wear a cap that has straps for attaching to the sealing flanges of the mask. The need for a cap and straps is very cumbersome and would be extremely uncomfortable to wear for extended periods of time. Also, the nasal mask of the '886 patent does not use nasal prongs, resulting in a patient not receiving a direct flow of oxygen into his/her nostrils.

Therefore, there is a need for a simple nasal mask assembly that is comfortable for a patient to wear for extended periods of time, is flexible such that it moves easily with a patient without moving or slipping out of position, is capable of providing a patient with a constant flow of oxygen, or other fluid, directly into the patient's nostrils, and does not interfere with the patient's eating or talking.

SUMMARY OF THE INVENTION

The present invention solves the problems associated with a conventional nasal cannula and prior art nasal masks by providing a nasal mask assembly that combines a nasal cup with nasal prongs. In particular, the nasal cup is made of clear plastic and has a general shape of a human nose such that it easily and comfortably fits over a patient's nose. An input port extends through the nasal cup wherein the input port has an internal end extending into the internal cavity of the nasal cup and to which the nasal prongs are attached, and an external end extending outward from the nasal cup and to which a fluid source is connected via a source tube system. The nasal prongs are about one inch in length, thereby extending well inside of the patient's nostrils so that oxygen flows directly into the patient's lungs.

A delivery tube optionally may be used to connect the internal end of the input port to the nasal prongs. The ends of the delivery tube may be open or closed. If the delivery tube ends are open, then the fluid flows through the nasal prongs, as well as, through the ends of the delivery tube into the internal cavity of the nasal cup. Therefore, a patient always receives a constant flow of fluid when breathing in through his/her nostrils.

A source tube system connected to the external end of the input port of the nasal cup is a system of tubing and connectors wherein a fluid source, e.g., an oxygen canister, is connected to the distal end of the tubing. The nasal mask assembly of the present invention also provides a means for rotating the source tube system about the external end of the input port. That is, the input port is a pivotal tube which allows the source tube system to rotate 360 degrees about the external end of the input port. The fact that the source tubing rotates about the input port provides a patient with additional comfort when wearing the nasal mask assembly and will provide the patient with constant delivery of oxygen directly into the nostrils even when the patient moves his/her head.

The nasal mask assembly also includes a means for securing the nasal cup over the patient's nose. In the preferred embodiment, the means for securing the nasal cup is a fastening mechanism connected to the sides of the nasal cup. For example, the fastening mechanism is two straps, one strap attached to each side of the nasal cup, adapted for securing together behind the patient's head. The straps are detachably secured together at their distal ends by conventional means, such as with detachable clips, hooks, VELCRO® hook and loop fasteners, or similar connectors. Furthermore, the straps are made of an elastic material in order to comfortably hold the nasal cup to the patient's head. In alternative embodiments, the means for securing is one strap that fits around the patient's head, one or more straps adapted for securing the nasal cup to a patient's ears, such as with eyewear, or an adhesive along the interior perimeter of the nasal cup.

Therefore, it is an object of this invention to provide a nasal mask assembly that combines the advantages of both a face mask and a nasal cannula.

It is another object of this invention to provide a moldable nasal cup such that the perimeter of the nasal cup can be molded to approximate the surface of a patient's face. A moldable nasal cup provides a more secure and comfortable seal of the nasal cup against the patient's skin.

It is another object of this invention to provide nasal prongs having an extended length over the prior art, thereby providing a patient with a secure fit and a means for directing a fluid, e.g., oxygen, directly into the patient's lungs.

It is another object of this invention to provide a means for rotating a source tube system at the connection with the input port of a nasal cup.

It is another object of this invention to provide a means for securing the nasal cup to a patient's head using one more straps or an adhesive.

It is another object of this invention to provide a nasal mask assembly that combines the advantages of both a face mask and a nasal cannula, while maintaining the patient's comfort and allowing the patient to speak and eat freely without interference.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

EMBODIMENTS OF THE INVENTION

Figure 1A:
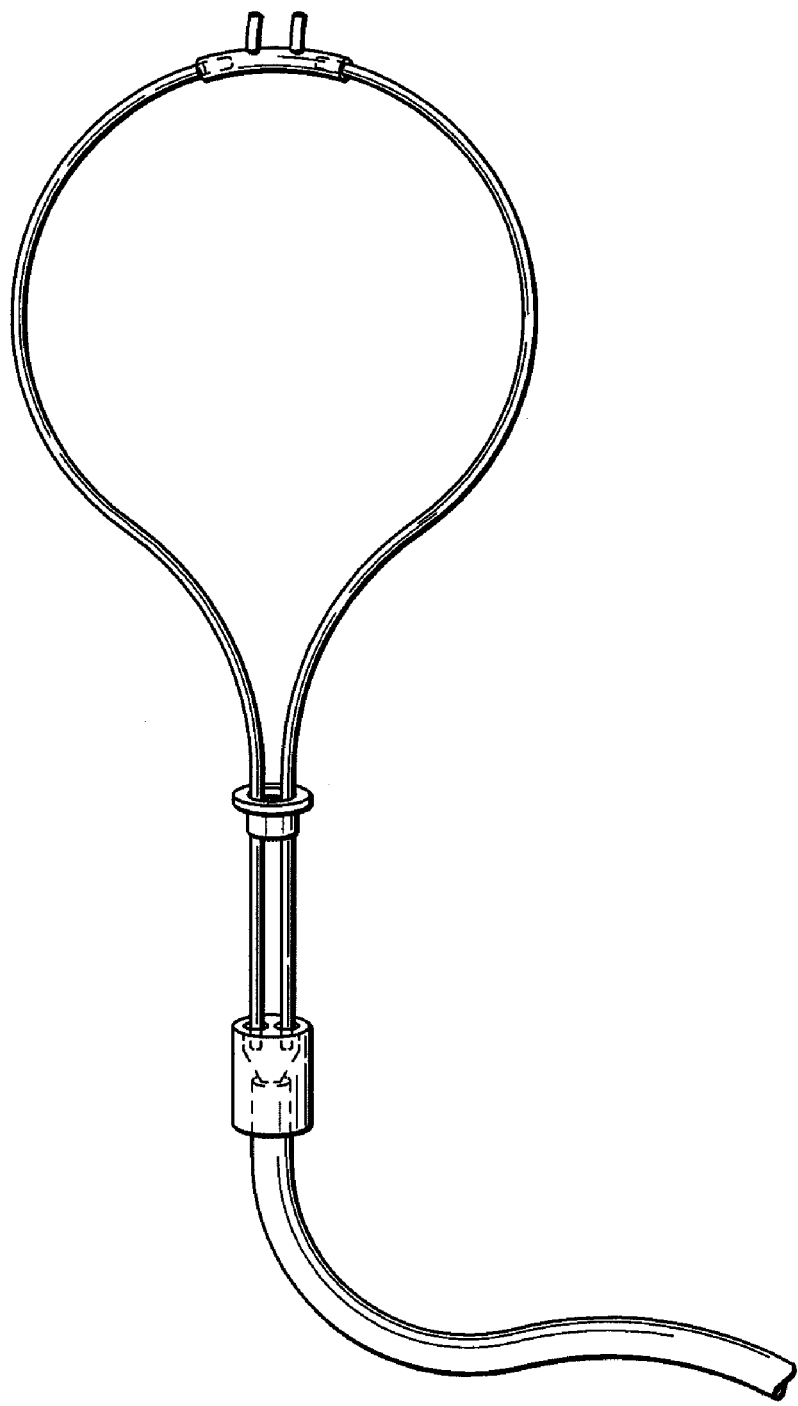
FIG. 1A is a perspective view of a prior art nasal cannula.
Figure 1B:
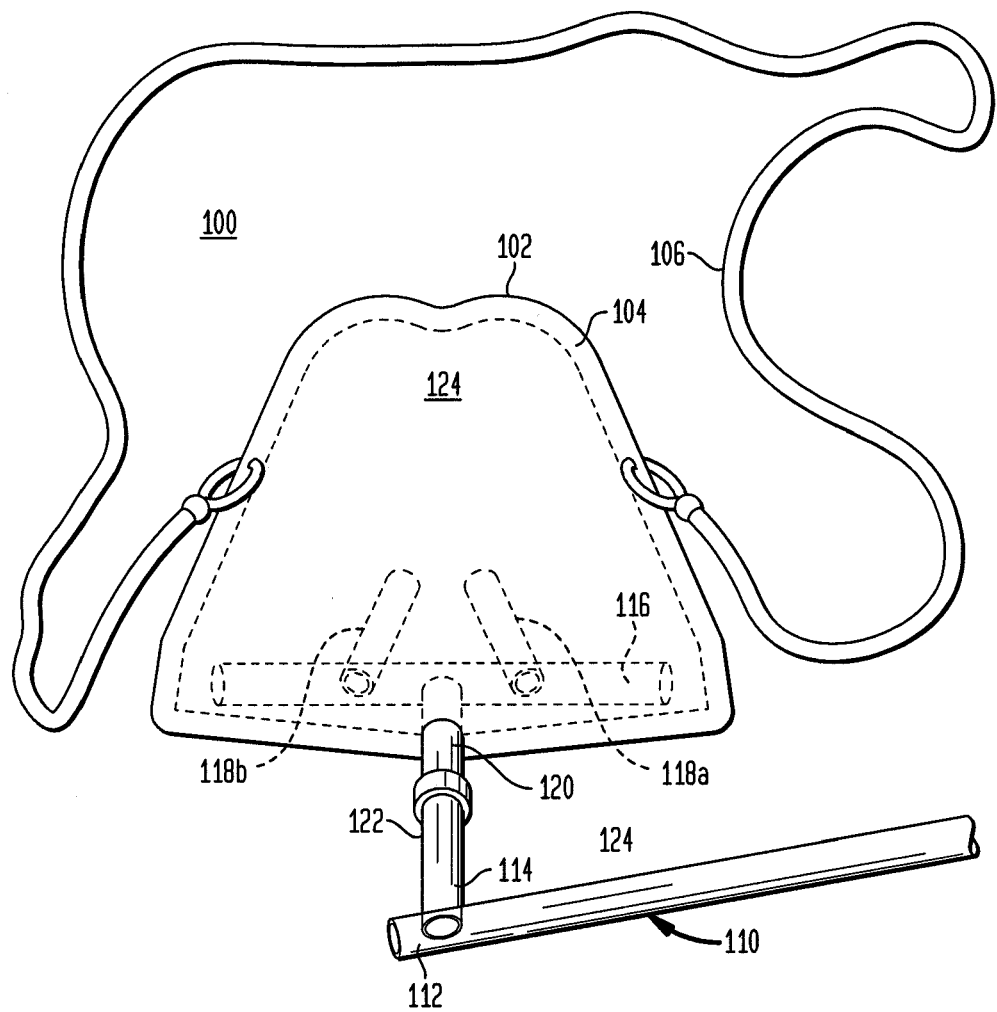
FIG. 1B is a perspective view of the front of a nasal mask assembly of one embodiment of the present invention.

As shown in the FIG. 1B and FIGS. 2-5, the present invention is a nasal mask assembly 100 for delivering a fluid from a fluid source 504 into a patient's 302 nostrils 306a and 306b. The present invention is described in terms of a patient 302 using the nasal mask assembly 100 for receiving a direct flow of oxygen, but this is for convenience purpose only. It would be readily apparent for one of ordinary skill in the relevant art to use the nasal mask assembly 100 of the present invention for delivering alternative fluids to a patient, such as, breathable air and an anesthesia.

In the preferred embodiment, the nasal mask assembly 100 comprises a nasal cup 102 adapted to cover a patient's 302 nose The nasal cup 102 is made of clear plastic and has a general shape of a human nose such that it has a perimeter and an internal cavity 124 that extends away from the patient's face and terminates at a distal end 304. An input port 122 extends through the nasal cup 102 into the internal cavity 124, wherein the input port 122 has an internal end 120 extending into the internal cavity 124 of the nasal cup 102 and an external end 114 extending outward from the nasal cup 102.

A nasal delivery system is in fluid communication with the internal end 120 of the input port 122 and is contained within the internal cavity 124 of the nasal cup 102. The nasal delivery system provides fluid, e.g., oxygen, directly into the patient's nostrils 306a and 306b. In the preferred embodiment, the nasal delivery system comprises a pair of nasal prongs 118a and 118b and a delivery tube 116, all of which are in fluid communication with the internal end 120 of the input port 122. In particular, the delivery tube 116 is generally horizontal in position, such that when a patient is wearing the nasal cup 102, the delivery tube 116 extends along a generally horizontal axis under his/her nose. The internal end 120 of the input port 122 is about centrally attached to the delivery tube 116. In addition, the ends of the delivery tube 116 are preferably open such that oxygen flowing through the nasal delivery system flows directly into the nasal prongs 118a and 118b, as well as, directly into in internal cavity 124 of the nasal cup 102. However, in an alternative embodiment, the ends of the delivery tube 116 may be closed.

The nasal prongs 118a and 118b are connected to the delivery tube 116 such that they extend away from the delivery tube 116 and into the internal cavity 124 of the nasal cup 102. The nasal prongs 118a and 118b may be straight or may have a slight curve to improve the comfort to a patient 302. The preferred length of each nasal prong 118a and 118b is about one inch in length, and the preferred distance between the nasal prongs 118a and 118b is about one half of an inch to about one inch. In addition, one nasal prong 118a is positioned on the delivery tube 116 on one side 202 of the input port 122, while the second nasal prong 118b is positioned on the delivery tube 116 on the second side 204 of the input port 122.

The delivery tube 116 is shown as being located along the bottom edge of the nasal cup 102 and as having a length about equal to the length of the bottom edge of the nasal cup 102, which is preferably about two inches in length, but this is for convenience. In an alternative embodiment, the delivery tube 116 may be shorter in length, such as the distal ends of the delivery tube 116 terminate at the nasal prongs 118a and 118b. In addition, the delivery tube 116 may have a different orientation, and be located elsewhere, within the nasal cavity 124. In another alternative embodiment, the nasal delivery system does not have a delivery tube 116 wherein the nasal prongs 118a and 118b are connected directly to the internal end 120 of the input port 122.

The nasal mask assembly 100 also includes a source tube system 110 in fluid communication with the external end 114 of the input port 122 of the nasal cup 102. That is, a first end 112 of the source tube system 110 is connected to, and is in fluid communication with, the external end 114 of the input port 122. A distal end of the source tube system 110 is connected to, and is in fluid communication with, the fluid source 504, e.g., an oxygen source. The fluid is delivered from the fluid source 504, through the source tube system 110 and input port 122, and into the patient's 302 nostrils 306a and 306b through the nasal prongs 118a and 118b. In the preferred embodiment, the source tube system 110 is a conventional oxygen delivery tube having a connector 506 on its distal end for connecting to an oxygen tank. The source tube system 110 also has one or more tube connectors 502 and one more sections of tubing 508a and 508b as needed to reach a desired length of tubing between the patient 302 and the fluid source 504.

In the preferred embodiment, the nasal mask assembly 100 further comprises a means for rotating the source tube system 110 about the external end 114 of the input port 122 of the nasal cup 102. In this embodiment, the input port 122 is a pivotal tube which allows the first end 112 of the source tube system 110 to rotate 360 degrees about the external end 114 of the input port 122.

Figure 2:
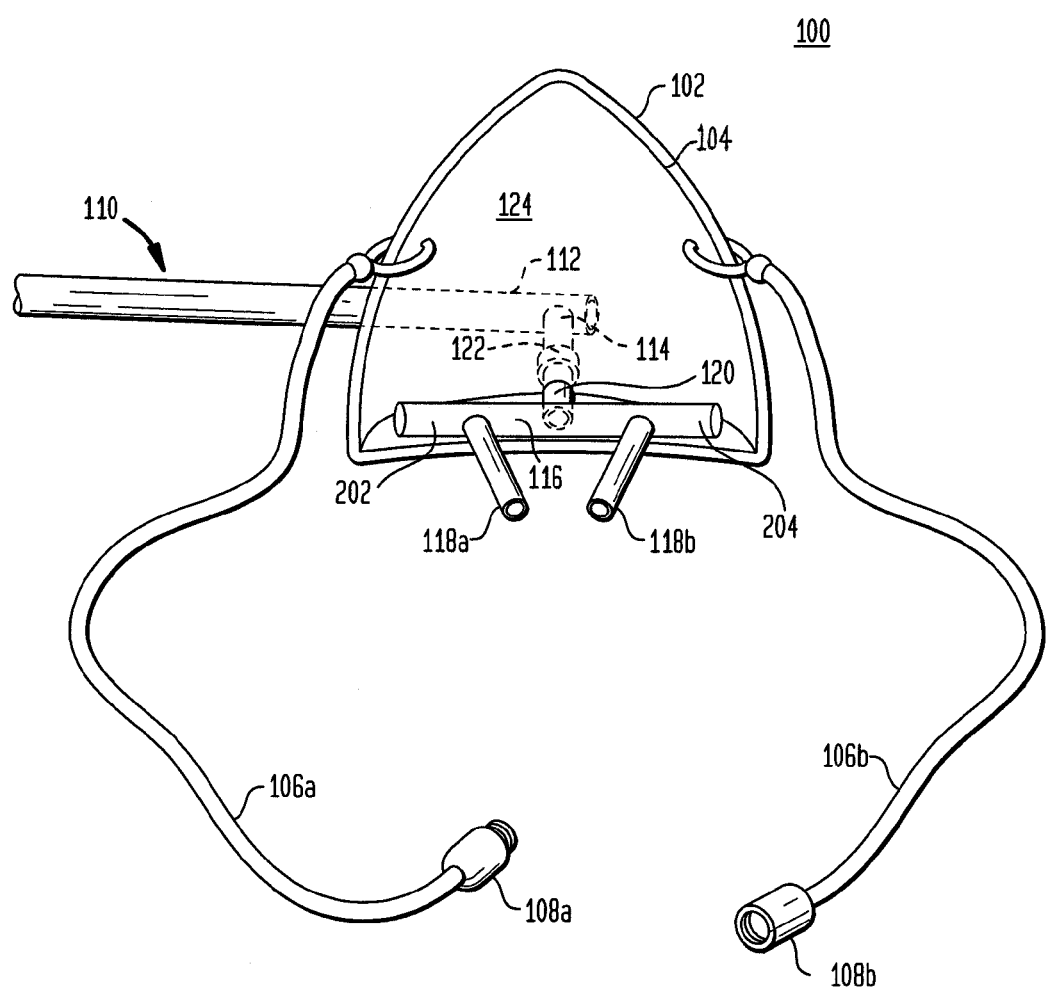
FIG. 2 is a perspective view of the back of the nasal mask assembly.
Figure 3:
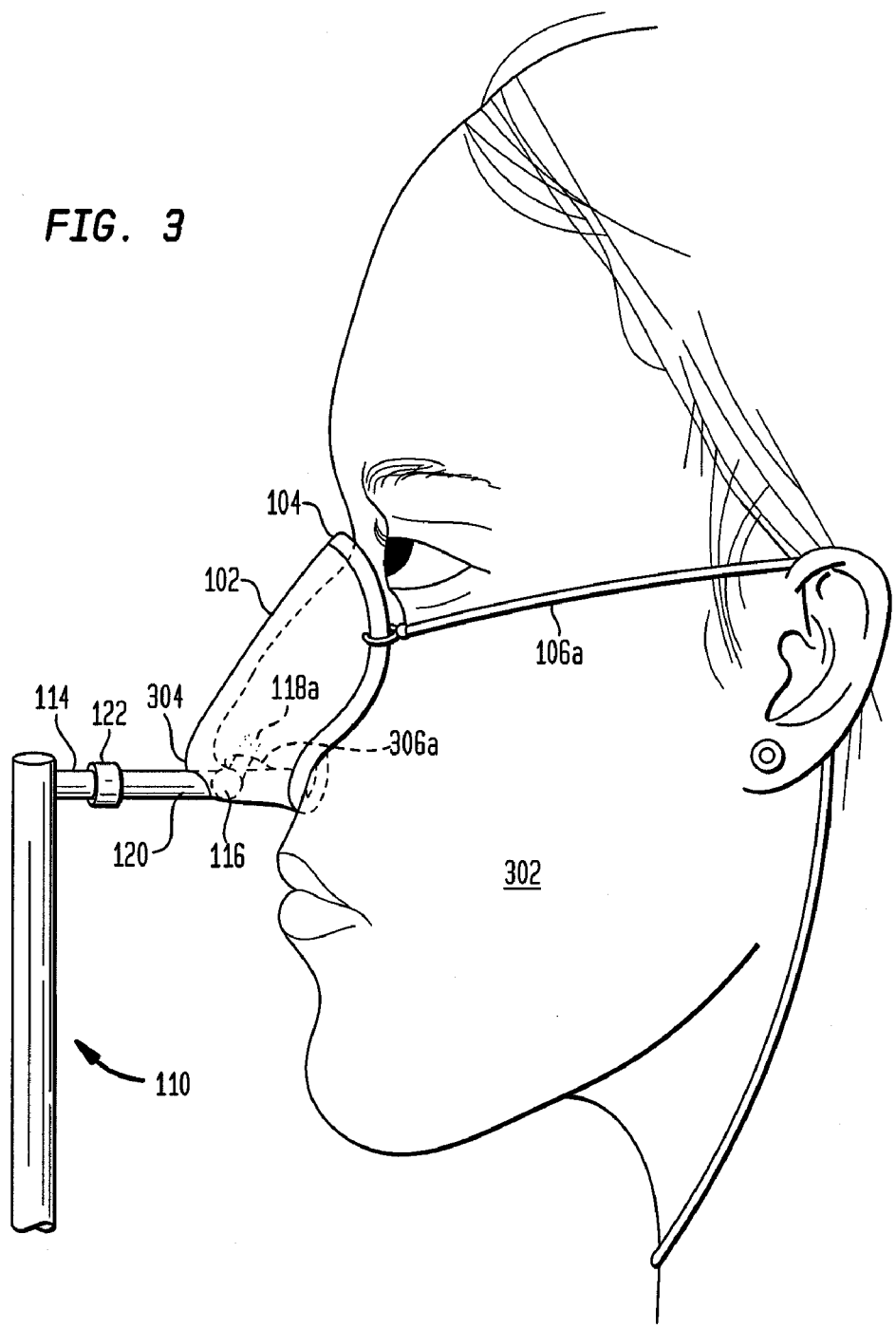
FIG. 3 is a perspective view of a side of the nasal mask assembly on a patient.
Figure 4:
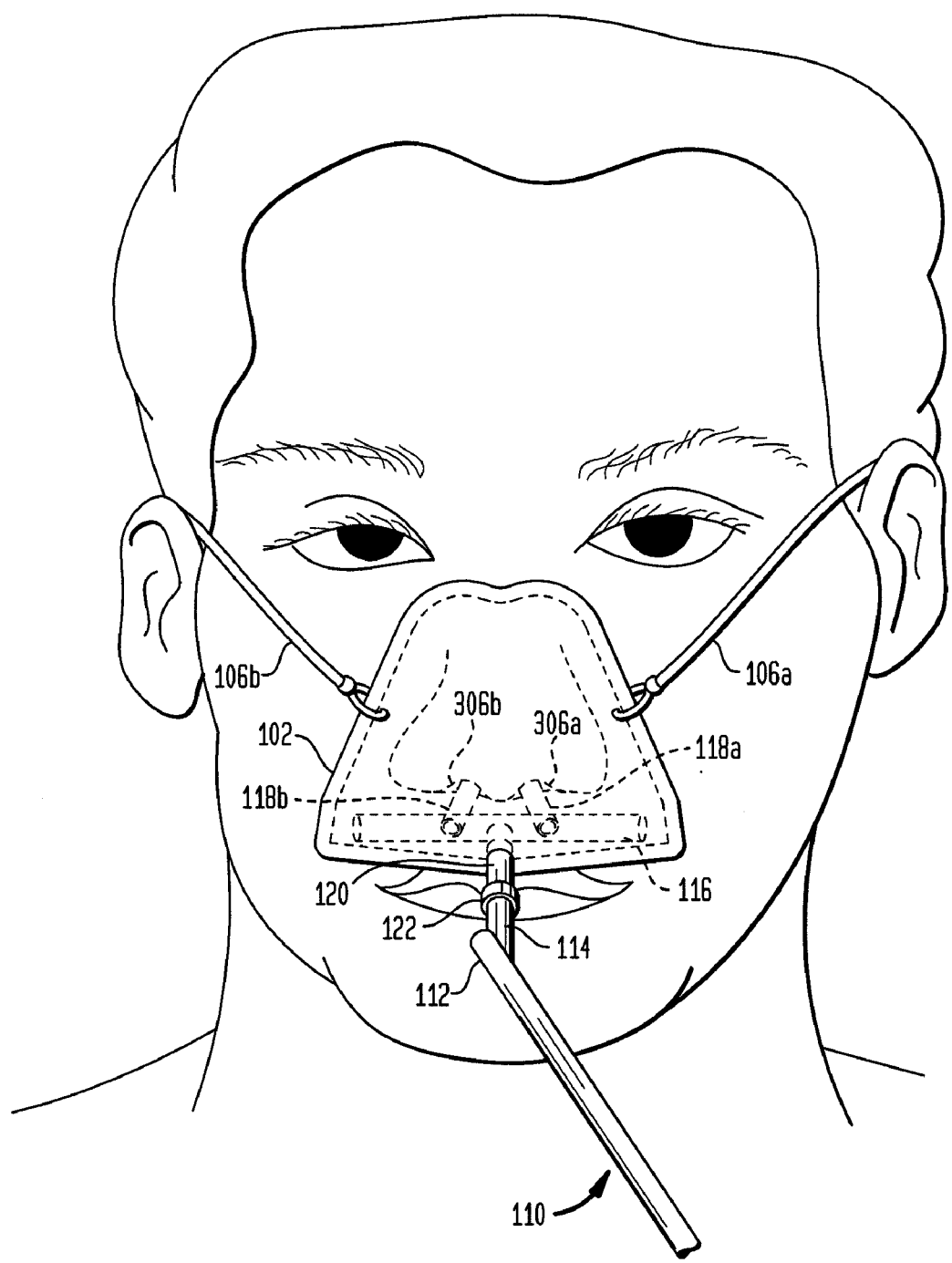
FIG. 4 is a perspective view of the front of the nasal mask assembly on the patient.
Figure 5:
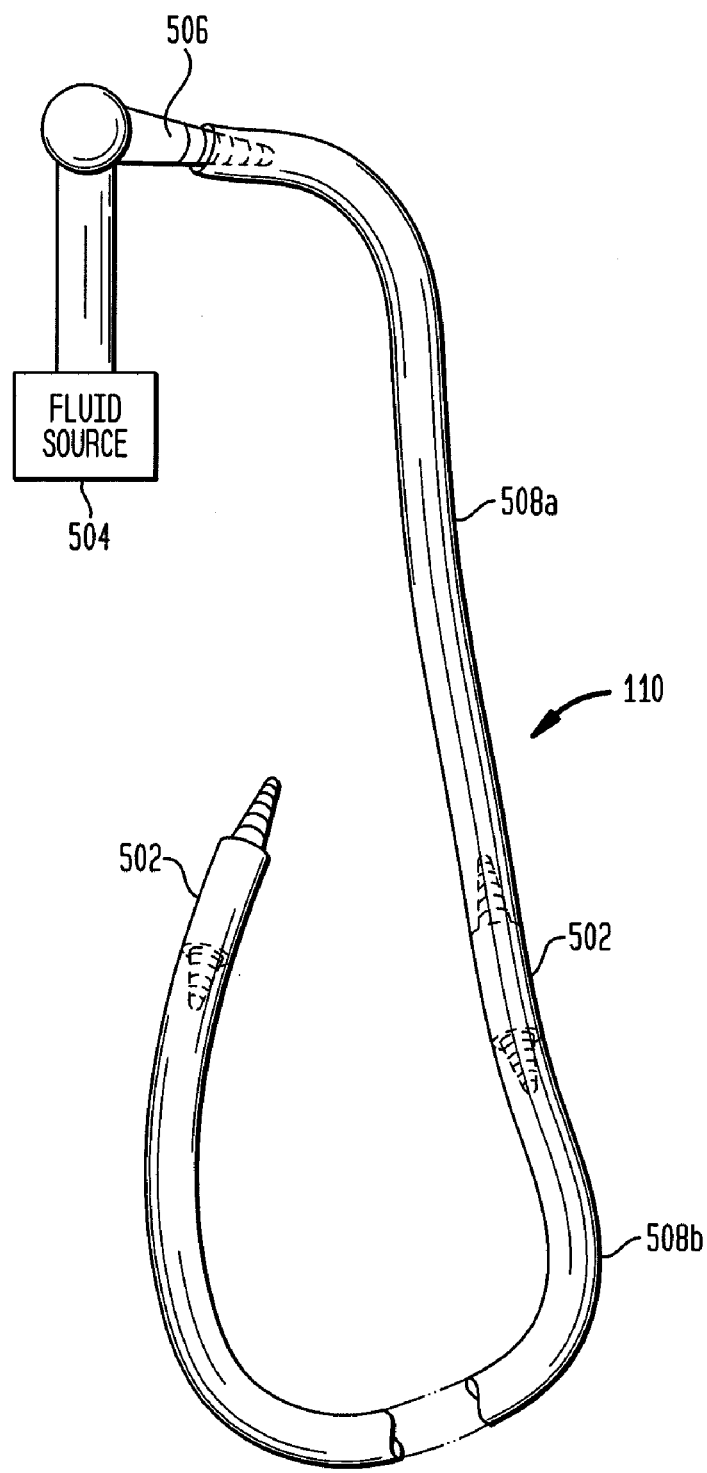
FIG. 5 is a perspective view of a source tube system connecting an input port of the nasal mask assembly to a fluid source.

The nasal mask system 100 also includes a means for securing the nasal cup 102 over the patient's 302 nose. In the preferred embodiment, the means for securing the nasal cup 102 is a fastening mechanism connected to the nasal cup 102. As shown in FIG. 2, the fastening mechanism may be two straps 106a and 106b adapted for fitting behind a patient's 302 head. A first strap 106a is attached to one side of the nasal cup 102, while a second strap 106b is attached to the second side of the nasal cub 102. The straps 106a and 106b are removably secured together at their distal ends by conventional means, such as by tying or with detachable clips, hooks, VELCRO® hook and loop fasteners, or similar connectors, e.g., connectors 108a and 108b. Furthermore, the straps 106a and 106b are made of an elastic material in order to hold the nasal cup 102 comfortably to the patient's 302 head. In alternative embodiments, the means for securing is one strap 106 that fits around the patient's 302 head, as in FIG. 1B, one or more straps adapted for securing the nasal cup 102 to a patient's 302 ears, such as with eyewear, or an adhesive along the interior perimeter of the nasal cup 102.

The preferred nasal mask assembly 100 also comprises a means for molding the perimeter of the nasal cup 102 to approximate a surface of the patient's 302 face surrounding the patient's 302 nose. That is, one or more thin strips of moldable material 104, e.g., metal, are attached along the interior perimeter of the nasal cup 102. The moldable material 104 may extend along the entire perimeter of the nasal cup 102, or may only extend around the sides and top of the nasal cup 102. Likewise, the moldable material 104 may be parallel to, below, or above the delivery tube 116 located along the bottom edge of the nasal cup 102. The moldable material 104 may be embedded within the perimeter of the mask cup 102 or may be attached along the internal or external surface of the nasal cup 102. Furthermore, the mask cup 102 itself may be made of a moldable material such that the entire mask cup 102 is molded by exerting pressure against the surface of the mask cup 102.

In operation, a patient 302 places a mask cup 102 of the present invention over his/her nose, and once it is in property position, the patient 302 bends the means for molding, e.g., the metal strip(s) 104 such that the perimeter of the nasal cup 102 follows the contours of his/her face. This molding of the perimeter of the nasal cup 102 ensures a close fit against the patient's skin, thereby maximizing the benefits of the oxygen being delivered to the patient 302. Then, while placing the nasal cup 102 over his/her nose a second time, the patient inserts the nasal prongs 118a and 118b into her/her nostrils and secures the straps 106a and 106b around his/her head. The fluid source system 110 is connected to the external end 114 of the input port 122 while its distal end is connected to a fluid source 504. Once completely connected, the fluid source 504 is engaged, thereby providing the patient 302 with a direct supply of the fluid, e.g., oxygen.

CONCLUSION

While various embodiments of the present invention have been described above, it should be under-stood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A nasal mask assembly for delivering a fluid from a fluid source into a patient's nostrils, comprising:
  a nasal cup adapted to cover a patient's nose, said nasal cup having a perimeter, an internal cavity, an input port having an internal end within said internal cavity of said nasal cup and an external end external to said nasal cup, and a nasal delivery system in fluid communication with said internal end of said input port and contained within said internal cavity, wherein said nasal delivery system comprises a pair of nasal prongs in fluid communication with said internal end of said input port, said nasal prongs having an outer diameter less than the inner diameter of the patient's nostrils and extending into the patient's nostrils, said nasal cup and said nasal prongs adapted to simultaneously deliver the fluid from said internal cavity of said nasal cup and said nasal prongs to the patient;
  a source tube system in fluid communication with said external end of said input port of said nasal cup and adapted to be in fluid communication with the fluid source such that the fluid is delivered from the fluid source to inside of the patient's nostrils through said nasal prongs of said nasal delivery system; and
  a means for securing said nasal cup over the patient's nose.

2. The nasal mask assembly according to claim 1, wherein the fluid is selected from the group consisting of breathable air, oxygen, and an anesthesia.

3. The nasal mask assembly according to claim 1, wherein said means for securing said nasal cup over the patient's nose is a fastening mechanism connected to said nasal cup.

4. The nasal mask assembly according to claim 3, wherein said fastening mechanism is selected from a group consisting of one or more straps adapted for fitting behind a patient's head, one or more straps adapted for securing said nasal cup to a patient's ears, and an adhesive along an interior of said perimeter of said nasal cup.

5. The nasal mask assembly according to claim 1, further comprising a means for molding said perimeter of said nasal cup to approximate a surface of the patient's face surrounding the patient's nose.

6. The nasal mask assembly according to claim 5, wherein said means for molding is one or more strips of moldable material positioned along said perimeter of said nasal cup.

7. The nasal mask assembly according to claim 6, wherein said moldable material is metal.

8. The nasal mask assembly according to claim 5, wherein said means for molding comprises said nasal cup being made of a moldable material.

9. The nasal mask assembly according to claim 1, further comprising a means for rotating said source tube at said external end of said input port of said nasal cup.

10. The nasal mask assembly according to claim 9, wherein said source tube rotates 360 degrees about said external end of said input port of said nasal cup.

11. The nasal mask assembly according to claim 9, wherein said input port is a pivotal tube.

12. The nasal mask assembly according to claim 1, wherein said nasal delivery system further comprises a delivery tube in fluid communication with said internal end of said input port and said nasal prongs.

13. The nasal mask assembly according to claim 12, wherein said delivery tube is generally horizontal and said internal end of said input port is about centrally attached to said delivery tube.

14. The nasal mask assembly according to claim 12, wherein said delivery tube has open ends in fluid communication with said internal cavity of said nasal cup.

15. The nasal mask assembly according to claim 1, wherein said nasal cup has a general shape of a human nose.

16. The nasal mask assembly according to claim 1, wherein said nasal cup is made of clear plastic.

17. The nasal mask assembly according to claim 1, wherein said nasal prongs are at least about one inch in length.

18. A method for delivering a fluid from a fluid source into a patient's nostrils, comprising the steps of:
 (a) providing a nasal mask assembly, comprising:
  a nasal cup adapted to cover a patient's nose, said nasal cup having a perimeter, an internal cavity, an input port having an internal end within said internal cavity of said nasal cup and an external end external to said nasal cup, and a nasal delivery system in fluid communication with said internal end of said input port and contained within said internal cavity, wherein said nasal delivery system comprises a pair of nasal prongs in fluid communication with said internal end of said input port, said nasal prongs having an outer diameter less than the inner diameter of the patient's nostrils and extending into the patient's nostrils;
  a source tube system in fluid communication with said external end of said input port of said nasal cup and adapted to be in fluid communication with the fluid source such that the fluid is delivered from the fluid source to the patient's nostrils through said nasal prongs of said nasal delivery system; and
  a means for securing said nasal cup over the patient's nose;
 (b) inserting said nasal prongs of said nasal mask assembly to inside of the patient's nostrils;
 (c) securing said nasal cup of said nasal mask assembly over the patient's nose;
 (d) connecting said source tube system to said external end of said input port of said nasal mask assembly;
 (e) connecting a distal end of said source tube system to the fluid source; and
 (f) simultaneously delivering fluid from the fluid source to the inside of the patient's nostrils from said internal cavity of said nasal cup and said nasal prongs of said nasal delivery system of said nasal mask assembly.

19. The method according to claim 18, wherein the fluid is selected from the group consisting of breathable air, oxygen, and an anesthesia.

20. The method according to claim 18, wherein said means for securing said nasal cup over the patient's nose is a fastening mechanism connected to said nasal cup.

21. The method according to claim 20, wherein said fastening mechanism is selected from a group consisting of one or more straps adapted for fitting behind a patient's head, one or more straps adapted for securing said nasal cup to a patient's ears, and an adhesive along an interior of said perimeter of said nasal cup.

22. The method according to claim 18, wherein said nasal mask assembly further comprises a means for molding said perimeter of said nasal cup to approximate a surface of the patient's face surrounding the patient's nose, and the method further comprises the step of:
 (g) molding said means for molding such that said perimeter of said nasal cup approximates the surface of the patient's face surrounding the patient's nose, wherein said step (g) is performed prior to said step (c).

23. The method according to claim 22, wherein said means for molding is one or more strips of moldable material positioned along said perimeter of said nasal cup.

24. The method according to claim 23, wherein said moldable material is metal.

25. The method according to claim 22, wherein said means for molding comprises said nasal cup being made of a moldable material.

26. The method according to claim 18, wherein said nasal mask assembly further comprises a means for rotating said source tube at said external end of said input port of said nasal cup.

27. The method according to claim 26, wherein said source tube rotates 360 degrees about said external end of said input port of said nasal cup.

28. The method according to claim 26, wherein said input port is a pivotal tube.

29. The method according to claim 18, wherein said nasal delivery system further comprises a delivery tube in fluid communication with said internal end of said input port and said nasal prongs.

30. The method according to claim 29, wherein said delivery tube is generally horizontal and said internal end of said input port is about centrally attached to said delivery tube.

31. The method according to claim 29, wherein said delivery tube has open ends in fluid communication with said internal cavity of said nasal cup.

32. The method according to claim 18, wherein said nasal cup has a general shape of a human nose.

33. The method according to claim 18, wherein said nasal cup is made of clear plastic.

34. The method according to claim 18, wherein said nasal prongs are at least about one inch in length.

\* \* \* \* \*